(12) United States Patent
Richardson (10) Patent No.: US 10,307,497 B2
(45) Date of Patent: Jun. 4, 2019

(54) CLO$_2$ ON DEMAND DISINFECTANT SPONGE OR WIPE AND METHOD OF MAKING (71) Applicant: University of Florida Research Foundation, Inc., Gainesville, FL (US)

(72) Inventor: David Ernest Richardson, Gainesville, FL (US)

(73) Assignee: University of Florida Research Foundation, Inc., Gainesville, FL (US)

(*) Notice: Subject to any disclaimer, the term of this patent is extended or adjusted under 35 U.S.C. 154(b) by 108 days.

(21) Appl. No.: 15/318,050

(22) PCT Filed: Jun. 11, 2015

(86) PCT No.: PCT/US2015/035259
§ 371 (c)(1),
(2) Date: Dec. 12, 2016

(87) PCT Pub. No.: WO2015/191811
PCT Pub. Date: Dec. 17, 2015

(65) Prior Publication Data
US 2017/0119916 A1 May 4, 2017

Related U.S. Application Data

(60) Provisional application No. 62/010,534, filed on Jun. 11, 2014.

(51) Int. Cl.
*C04B 35/00* (2006.01)
*B01D 11/02* (2006.01)
(Continued)

(52) U.S. Cl.
CPC ............... *A61L 2/18* (2013.01); *A01N 59/00* (2013.01); *A61L 2/232* (2013.01); *A61L 2/235* (2013.01);
(Continued)

(58) Field of Classification Search
CPC .................... C01B 11/024; B01J 31/2295
(Continued)

(56) References Cited

U.S. PATENT DOCUMENTS 3,684,437 A 8/1972 Callerame
6,277,408 B1 * 8/2001 Wellinghoff ........... A01N 25/18
424/473
(Continued)

FOREIGN PATENT DOCUMENTS

EP 423816 A2 4/1991
EP 423817 A2 4/1991
(Continued)

*Primary Examiner* — Monzer R Chorbaji
(74) *Attorney, Agent, or Firm* — Thomas|Horstemeyer, LLP (57) ABSTRACT

A disinfectant appliance has a plurality of chlorite absorbent particles, a plurality of redox resin particles, and at least one absorbent material combined such that the absorbent material allows and can promote: infusion of water into the disinfectant appliance; release of the chlorite from the chlorite absorbent particles into the water to form a chlorite comprising solution; contacting of the chlorite comprising solution with the redox resin particles; and the expulsion of ClO$_2$ comprising solution from the disinfectant appliance onto a surface to be disinfected. The disinfectant appliance can include a storage section and can include a handle. The disinfectant appliance can be in the form of a wipe or sponge that can be contacted with a surface suspected of being infected.

24 Claims, 6 Drawing Sheets (51) Int. Cl.
| | |
|---|---|
| *A61L 9/00* | (2006.01) |
| *B32B 27/00* | (2006.01) |
| *A61L 2/18* | (2006.01) |
| *A61L 2/235* | (2006.01) |
| *A01N 59/00* | (2006.01) |
| *A61L 2/232* | (2006.01) |
| *C11D 17/04* | (2006.01) |

(52) U.S. Cl.
CPC ......... *A61L 2202/11* (2013.01); *C11D 17/049* (2013.01)

(58) Field of Classification Search
USPC ............... 252/62.51 C; 428/425.5; 423/477; 422/236, 5, 28, 36, 305; 424/473
See application file for complete search history.

(56) References Cited

U.S. PATENT DOCUMENTS

| | | |
|---|---|---|
| 6,764,661 B1 | 7/2004 | Girard |
| 7,087,208 B2 | 8/2006 | Sampson et al. |
| 7,824,556 B2 | 11/2010 | Sampson et al. |
| 7,964,138 B2 | 6/2011 | Richardson et al. |
| 8,323,563 B2 | 12/2012 | Richardson et al. |
| 2008/0292534 A1 | 11/2008 | Richardson |
| 2013/0017241 A1 | 1/2013 | Andrews et al. |
| 2013/0089473 A1 | 4/2013 | Schroeter et al. |

FOREIGN PATENT DOCUMENTS

| | | |
|---|---|---|
| WO | WO 1999/062817 | 12/1999 |
| WO | WO 2014/028485 | 2/2014 |
| WO | WO 2014/138000 | 9/2014 |

\* cited by examiner

$ClO_2$ ON DEMAND DISINFECTANT SPONGE OR WIPE AND METHOD OF MAKING

CROSS-REFERENCE TO RELATED APPLICATIONS

This application is the U.S. national stage application of International patent application No. PCT/US2015/035259, filed Jun. 11, 2015, which claims the benefit of U.S. Provisional Application Ser. No. 62/010,534, filed Jun. 11, 2014, the disclosures of which are hereby incorporated by reference in their entireties, including all figures, tables and drawings.

BACKGROUND OF INVENTION

Chlorine dioxide ($ClO_2$) is an agent that is used annually in the U.S. at a rate of approximately 4 million pounds per year, primarily for water purification and wood pulp bleaching as a replacement for chlorine/hypochlorite. Chlorine dioxide is an effective microbicide as a gas and in solution and also can destroy certain chemical substances and toxins. Chlorine dioxide has excellent environmental qualities, as it does not produce large quantities of chlorinated hydrocarbon byproducts. Many processes are known for the production of $ClO_2$ in gas or solution forms suitable for large-scale use. Typically, rather cumbersome equipment is needed to produce $ClO_2$ solutions, such as, electrolysis cells and DC power supplies for $ClO_2$ generation. Generally, the $ClO_2$ solution has a very finite lifetime and must be used approximately within the day it has been generated.

Chlorine dioxide solutions can be produced by treatment of chlorite salt solutions (e.g., $NaClO_2$) with a strong acid to produce acidic solutions that contain $ClO_2$. Ion exchange media can be used for the formation of chlorine dioxide; for example, Callerame, U.S. Pat. No. 3,684,437 discloses production of chlorine dioxide by ion exchange between a mixed bead cation-anion exchange resin and a chlorite of an alkali metal or an alkaline earth metal with a very slow flow rate. Similarly, U.S. Pat. Nos. 7,087,208 and 7,824,556, both to Sampson et al disclose generation of chlorous acid from a chlorite salt precursor by passing an aqueous solution of the precursor through a cationic ion exchange resin in a hydrogen ion (acid) form and a catalytic material to accelerate the decomposition of chlorous acid to chlorine dioxide using gravity feed at a moderate rate.

A method for $ClO_2$ production, which can be conveniently and safely performed using a redox-modified resin in conjunction with a chlorite precursor solution or absorbed chlorite and water that can be combined in a portable device, is disclosed in Richardson et al., U.S. Pat. Nos. 7,964,138 and 8,323,563 and Richardson, International Patent Application Publication Nos. PCT/US2013/054724, and PCT/US2014/020178. The devices disclosed therein are designed such that the reactive components are contained in separate containers until solution generation is desired. These methods require the feeding of liquid through one or more reactive beds to produce $ClO_2$ solutions. Although the method of Richardson et al. is useful for commercial and even portable emergency production of chlorine dioxide, the containment and storage of a relatively large amount of an isolated aqueous solution as the feed solution is required. Therefore, a method of retaining both complementary reagents in a bound state, such that any available water can be used as the liquid feed, rather than a specific precursor-containing solution, is desirable for reduction of the complexity and size of a chlorine dioxide generator.

Schroeter et al. U.S. Patent Application Publication No. 2013/0089473 teaches a device to facilitate the generation of $ClO_2$ where a chamber of $NaClO_2$ and a chamber of a solid dry acid are formed about a dissolvable barrier separating the two chambers. The device can be submerged in water in a container designed to hold a sufficient quantity to swell the contents of the chambers, which ultimately dissolve the barrier and mix the $ClO_2$ precursors to generate $ClO_2$ gas that diffuses from the device to introduce $ClO_2$ gas to a space to be disinfected or deodorized.

Andrews et al. U.S. Patent Application Publication No. 2013/0017241 teaches a $ClO_2$ generator that is in the form of a tablet or capsule where a core portion contains a solid acid and a metal chlorite dispersed in a porous solid vehicle and is covered with at least one protective layer that is water permeable, particularly a polyalkyleneoxide polyvinyl alcohol copolymer, over at least a portion of the core. The generator is placed in water to dissolve and mix the reactants, which liberates the $ClO_2$ from the core into solution or as a gas.

It is desirable to have a $ClO_2$ impregnated wipe for use for viral or bacterial disinfection or cleaning of contaminated surfaces. It is also desirable that the wipe can be activated with water and rather quickly generates $ClO_2$ solution for use on demand in a controlled manner at ambient room temperature.

DETAILED DISCLOSURE

Figure 1:
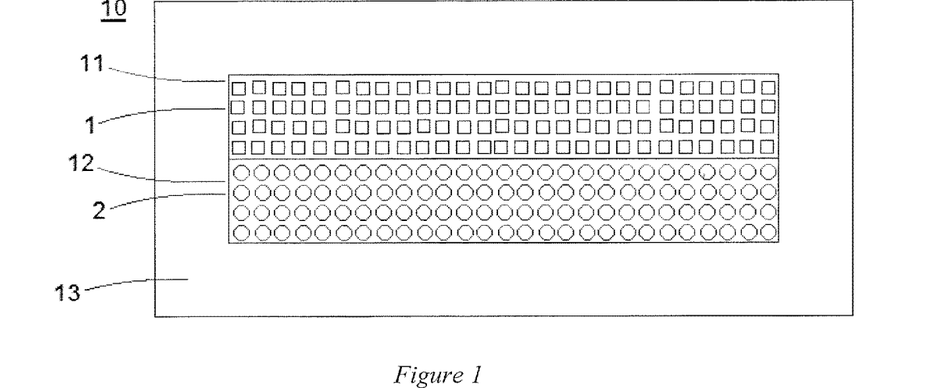
FIG. 1 shows a disinfectant appliance in the form of a sponge with a first layer comprising chlorite absorbent particles and a second layer comprising redox resin particles, according to an embodiment of the invention.
Figure 2:
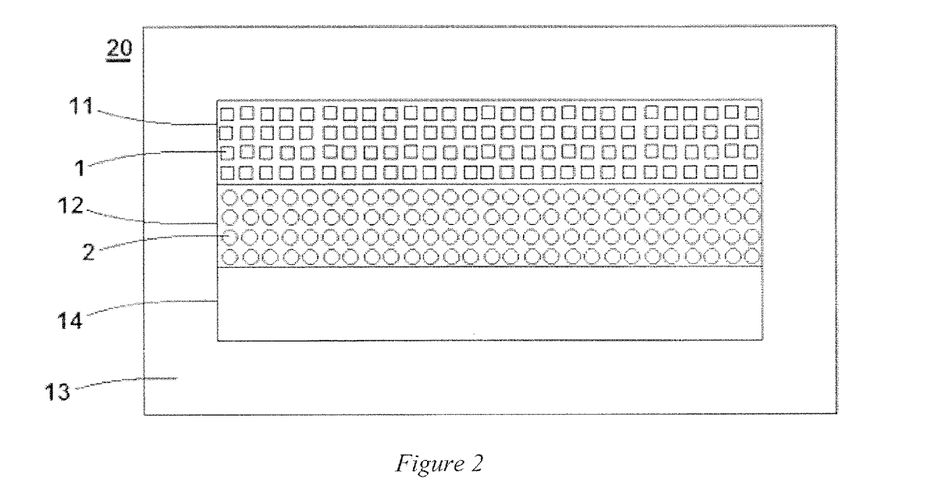
FIG. 2 shows a disinfectant appliance in the form of a sponge with a first layer comprising chlorite absorbent particles, a second layer comprising redox resin particles, and a storage section, according to an embodiment of the invention.
Figure 3:
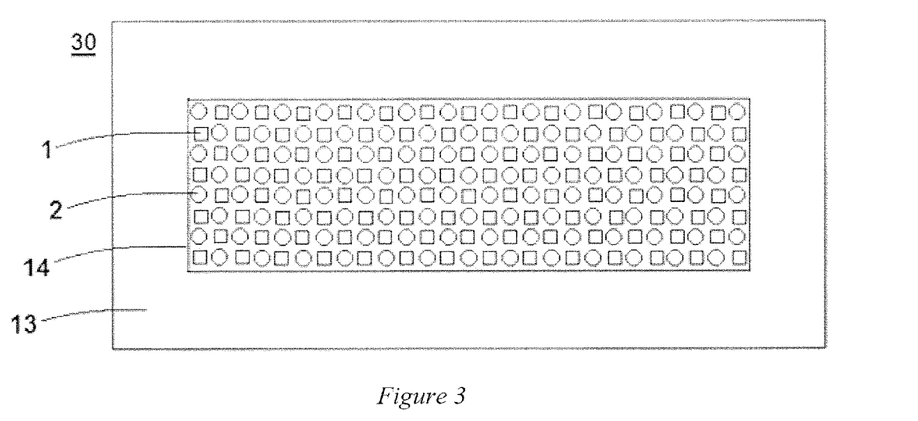
FIG. 3 shows a disinfectant appliance in the form of a sponge where chlorite absorbent particles and redox resin particles are dispersed within a combined layer, according to an embodiment of the invention.
Figure 4:
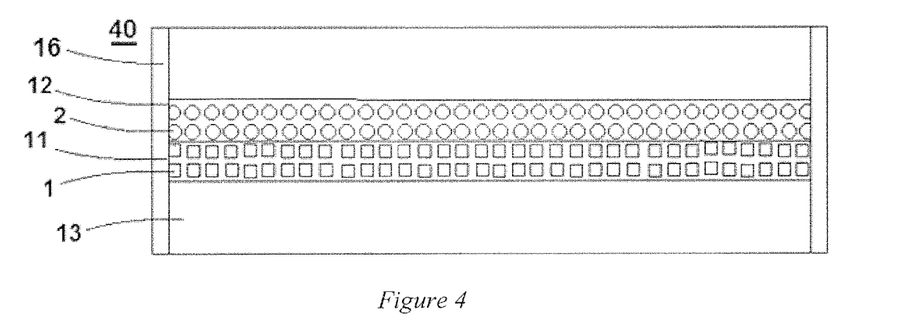
FIG. 4 shows a disinfectant appliance in the form of a wipe with a first layer comprising chlorite absorbent particles and a second layer comprising redox resin particles, according to an embodiment of the invention.

Embodiments of the invention are directed to disinfectant appliances and their uses, where a $ClO_2$ solution is formed when the appliance is wetted with water, water solution, or a solvent that can permit the dissolving of salts and $ClO_2$ and does not undergo reaction with the $ClO_2$ or the salts. Water is drawn into the appliance by capillary action from one or more exterior surfaces. Capillary action is normally used, for example, in sponges, which can absorb a significant amount of water relative to their weight. Sponges, wipes or other appliances can be fabricated with a wide variety of shapes and sizes. For example, the wipe can be towel-like of various dimensions and can use polymeric structural materials including cellulose materials, such as a paper towel. The adsorbent appliance contains absorbed chlorite and a redox-modified resin or an acid resin, and is in a relatively anhydrous state; one where there is no possible flow of water in a liquid state, prior to contacting with water. Water drawn into the appliance dissolves the absorbed chlorite to form a chlorite solution that subsequently comes into contact with the redox resin or acid resin. As disclosed herein, most embodiments of the invention are described using a redox resin, which has some kinetic advantages over acid resins and permits more neutral pH solutions to be formed; however, it should be understood that the redox resin can be replaced with an acid resin, in embodiments of the invention. As illustrated in FIG. 1, in an embodiment of the invention, where the appliance 10 is a sponge, water is drawn into the device by the surface layer 13 and passes through a first layer 11 of the appliance that contains chlorite absorbent particles 1, which are particles that absorb chlorite salt; and the resulting chlorite containing solution that is formed passes through a second layer 12 of the appliance that contains redox resin 2. Alternatively, the first layer 11 and the second layer 12 can be of materials that inherently absorb chlorite salt and act as a redox reagent binder, respectively. In all embodiments of the invention, any layer that supports particles can be replaced with a supporting material that functions in the manner in which the imbedded particles are described in addition to acting as a structural material that permits the flow of water or other solvent through the appliance. For example, the redox resin can be replaced with a cross-linked material that has water absorbency and contains material bound cations to function as an anion exchange material in the manner of traditional anion exchange resins disclosed herein. For example, the chlorite absorbent particles can be replaced with a cross-linked material that has functionality the can reversibly absorb a chlorite salt. The thicknesses of layers and all other dimensions of the appliances and all relative dimensions, as shown in FIG. 1 or any other figure, are for illustration purposes only and the dimensions shown are not intended to limit the appliances, according to embodiments of the invention. For example, in a towel-like wipe, the thickness can be less than $\frac{1}{100}^{th}$ of the smaller of the other dimensions, whereas, in a cubic sponge, all dimensions are equal. In another embodiment of the invention, the chlorite absorbent particles 1 and redox resin 2 may be interspersed in a combined layer 14 with adsorbent material of the sponge 20, as shown in FIG. 2. Optionally, the resulting $ClO_2$ solution can be adsorbed in a storage section 15, as shown in FIG. 3, which allows a substantial amount of $ClO_2$ solution to be held for a short duration or used immediately after wetting of the appliance 30. These capillary action driven appliances avoid use of separate generators for $ClO_2$ solutions and allow the handling of $ClO_2$ solution in a wetted sponge 10, as in FIG. 1, or in a wetted wipe 40, as shown in FIG. 4, where parallel layers are overlaid and sealed by a seal 16 that can be a stitching or an adhesive seal. Sponges can be formed where two or more portions are attached using an adhesive. The disinfectant appliance, according to embodiments of the invention, is a convenient form for applying $ClO_2$ solution for disinfection and sanitation, including surface cleaning and wound care.

Figure 5:
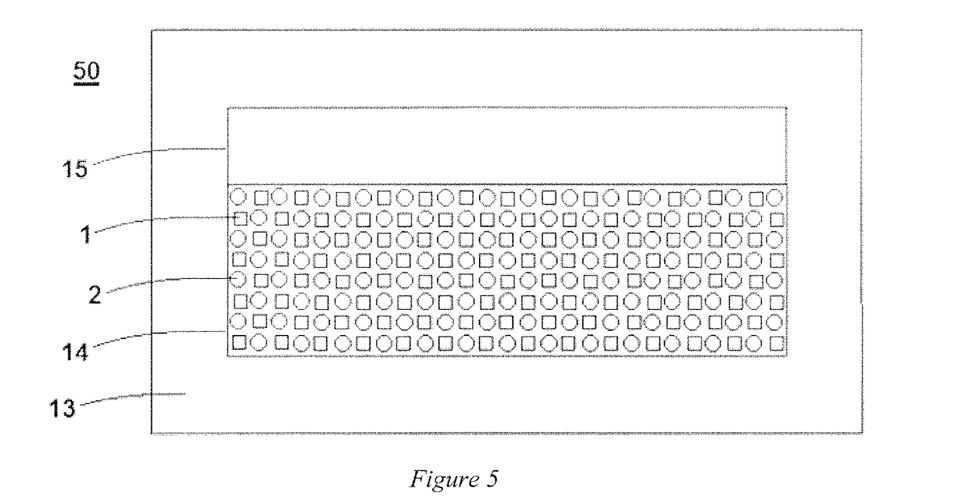
FIG. 5 shows a disinfectant appliance in the form of a sponge where chlorite absorbent particles and redox resin particles are dispersed within a combined layer and a storage section is disposed on a side of the combined layer, according to an embodiment of the invention.

As illustrated in FIGS. 1 and 2, it is desirable to introduce water from a surface proximal to the first layer 11 such that the water first contacts chlorite absorbent particles 1 prior to contacting the second layer 12 containing the redox resin 2. The $ClO_2$ solution storage section 14 resides on the side of the second layer 12 opposite that of the first layer 11 to promote water flow from absorbed chlorite to redox resin and then to storage. As shown in FIG. 5 for appliance 50, when the chlorite absorbent 1 and redox resin 2 are contained in a combined layer 14, it is advantageous for the water to be drawn into the appliance from the surface that obliges fluid flow through the combined layer 14 before fluid enters the storage section 15.

Figure 6:
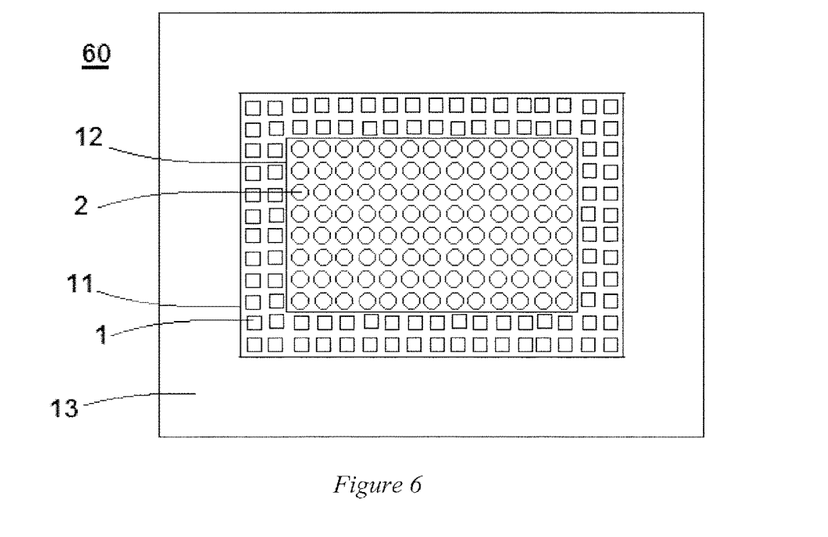
FIG. 6 shows a disinfectant appliance in the form of a sponge with a first layer comprising chlorite absorbent particles covering a core of a second layer comprising redox resin particles, according to an embodiment of the invention.
Figure 7:
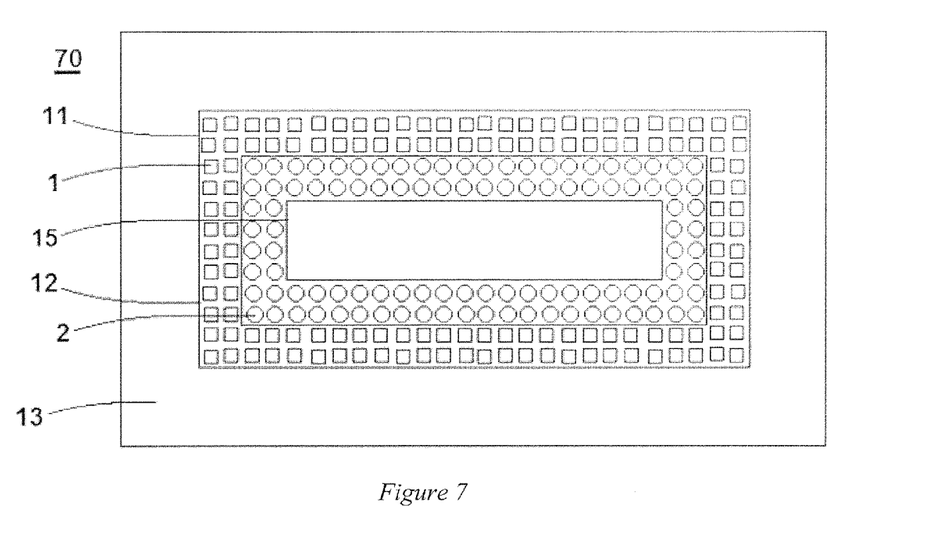
FIG. 7 shows a disinfectant appliance in the form of a sponge with a first layer comprising chlorite absorbent particles covering a second layer comprising redox resin particles that covers a core storage section, according to an embodiment of the invention.
Figure 8:
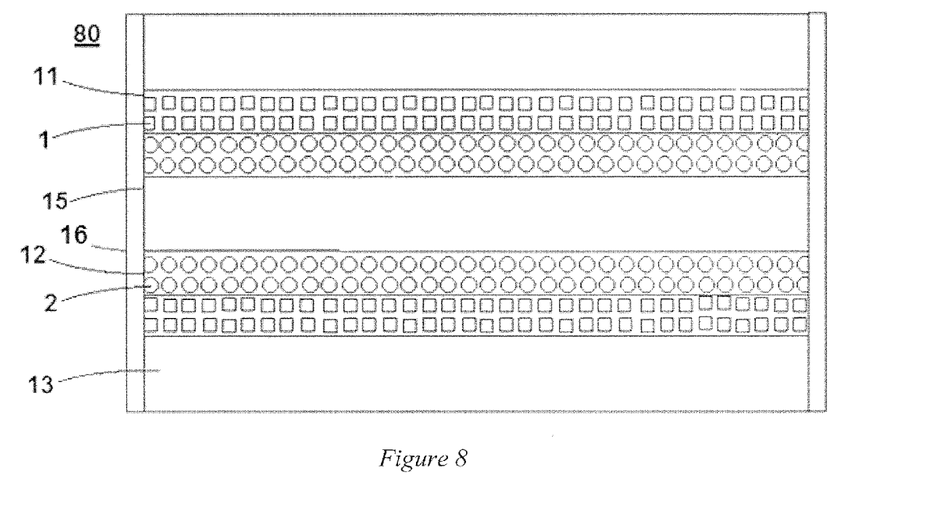
FIG. 8 shows a disinfectant appliance in the form of a wipe with a pair of first layers comprising chlorite absorbent particles and a pair of second layer comprising redox resin particles positioned on a central storage section, according to an embodiment of the invention.

In an embodiment of the invention, as shown in FIG. 6, in sponge 60 the second layer 12 containing redox resin 2, can be surrounded by the first layer 11 containing the chlorite absorbent. Such an appliance can be totally submerged in water and the water drawn from the surface layer 13 through the first layer 11 and into the second layer 12. As shown in FIG. 7, for sponge 70, a storage section 15 can be in the center of a sponge surrounded by the second layer 12. A storage section can be included in a wipe, for example as shown in FIG. 8, as a central storage section 15 in wipe 80 with two second layers 12 on opposing sides of the storage section 15, and with two first layers 11 situated on the exterior faces of the second layers 12, such that when submerged, the water is drawn into the wipe through the surface layers 13 to the central storage layer 15.

In an embodiment of the invention, a porous silica gel support is contacted with a concentrated sodium chlorite solution, or any other aqueous solution of any water soluble chlorite salt, where the chlorite solution is absorbed into the micro-channels within the silica gel to form the chlorite absorbent particles. The silica gel support and the resulting chlorite absorbent particle can be in the form of free flowing beads, powders, or any other form that readily permits the flow of water through the layer of the silica gel. The sodium chlorite impregnated silica gel can have a sufficient portion of the water removed from the chlorite absorbent, as desired, such that the silica gel behaves as a non-wetting and non-leaking layer during construction and distribution of the disinfectant appliance prior to use. In this manner, a relatively high concentration of sodium chlorite, or other soluble metal chlorite, such as, for example, potassium chlorite, lithium chlorite, cesium chlorite, magnesium chlorite, or calcium chlorite, can be loaded to a high level in a relatively free flowing particulate solid or continuous gel form. As a particulate solid, the particles can display dimensions from about 10 micrometers or less to about 1 millimeter or more in cross-section. The particulate matter can be spheres, rods, any other regular shape, or they can be irregular in shape. The particles can have a narrow size distribution or a broad size distribution.

In an embodiment of the invention, the sodium chlorite impregnated silica gel can be blended with other materials that permit the flow of water into and through the layer. Other materials included can be foams or polymeric gels that promote wicking or absorption of water into the layer and promote flow of the sodium chlorite solution from the absorbent of the chlorite comprising layer. The polymeric gels can include water absorbent materials with at least a hydrophilic surface that allow or promote the absorption of water into the layer and not impede the transport of the sodium chlorite solution out of the layer. The foam or gel materials can be, for example, polyesters, polyurethanes, polyamides, polyolefins, polydimethylsiloxane, celluloses, polyvinyl alcohol, any combination thereof, or any other material that can be employed as a liquid permeable layer comprising the sodium chlorite impregnated silica. Typically, but not necessarily, a foam is an open cell foam. Any foam manufacturing method can be employed that permits the formation of a pocket, or the filling of the foam precursor with the chlorite impregnated silica or any other absorbent, such as alumina, titania, or other metal oxide, and carrying out the foaming without the release or reaction of the chlorite being absorbed. The exterior surface layer of a sponge can be foam that allows the inclusion of water, swelling to 5, 10, 15, 20, 25 or more times the dry foams dimensions. When included, the storage section of a disinfectant appliance can be the same, similar, or different foam than the exterior surface, or can be an empty cavity within the appliance.

In embodiments of the invention, the second layer comprising a redox resin is formed where an anion exchange resin in a $Br_3^-$, $Cl_3^-$, or any anionic tri-halogen form, for example, $IBr_2^-$, $ICl_2^-$, $BrI_2^-$, $BrCl_2^-$, $BrI_2^-$, $ClBr_2^-$, or $ClI_2^-$, is included. For example, $Br_3^-$ can be bound to an ion exchange resin by passing a bromine water solution through an anionic exchange resin with bound $Br^-$ ions. For example, an Amberlite™ anion exchange or resin in the $Cl^-$ form is washed with dilute hydrochloric acid and subsequently with a NaBr solution to achieve a $Br^-$ bound resin. After washing free $Br^-$ from the resin with water, saturated aqueous bromine can be washed through the $Br^-$ bound resin and subsequently washed with water to form a $Br_3^-$ bound resin. In another embodiment of the invention, a $Cl_3^-$ bound resin can be formed in the manner disclosed in Richardson, International Patent Application Publication No. WO/2014/028485, which is incorporated herein by reference. The resin can be in the form of beads or of a powder and can be sufficiently dried such that, upon construction of the dry disinfectant appliance, water leakage does not occur. The form of the resin can be beads or powder where it is placed in a layer, which can include a foamed or gelled supporting material that permits delivery of water to the resin or powder upon wetting of the wipe or sponge. Supporting materials freely permit water to flow into intimate contact with the redox resin and chlorite absorbent to allow their position and distribution to remain in a desired orientation after production and remain so through distribution and during use of the appliance.

In embodiments of the invention, the redox resins can be replaced with acid resins. For example, an acidic cation exchange resin, which is a resin being functionalized to exchange hydrogen ions, $H^+$, for other cations in solutions (e.g. Dowex™ from Dow Chemical) is used rather than a redox resin. In this manner, the resulting $ClO_2$ comprising solution is acidic in nature because $HClO_2$ is formed by the proton exchange, which decomposes to $ClO_2$ by the reaction:

$$5HClO_2 \rightarrow 4ClO_2 + HCl + 2H_2O.$$

In other embodiments of the invention, the absorbed chlorite salt can be replaced with a chlorite bound ion exchange resin where, rather than using water, a salt solution, for example, a sodium chloride solution can be passed through the chlorite bound ion exchange resin to release chlorite anions into solution. In another embodiment of the invention, the redox resin can be replaced with the chlorite bound anion exchange resin and the absorbed chlorite salt can be replaced with an absorbed acid or an acid anhydride that delivers acid to the chlorite bound ion exchange resin to form $HClO_2$ solution.

A storage section can be formed in the disinfectant appliance to exclusively absorb $ClO_2$ comprising solution. The storage section can promote flow through the one or more layers that contain chlorite absorbent and/or redox resin. The storage section can consist of an open foam, where $ClO_2$ comprising solution wicks into this $ClO_2$ absorption layer. The layer must be effectively unreactive with the $ClO_2$ for the duration between the wetting of the wipe or sponge and the expelling of the $ClO_2$ solution from the disinfectant appliance.

The storage section or any other component section may be initially compressed to reduce the size of the appliance to facilitate efficient storage, packaging and transport. Upon adsorption of liquid, the compressed layer will expand to a final size that is larger than the original appliance and has a larger capacity than an uncompressed appliance.

An embodiment of the invention is directed to a method for the use of the disinfectant appliance. The use begins when water contacts the appliance. Water is wicked from the outside surface of the wipe or sponge when submerged in water or otherwise contacted with water, for example, held under running water for a controlled period of time, where water is poured onto the sponge or wipe, or where water is sprayed onto a surface to be decontaminated and the wipe is placed on the wet surface. Depending upon the dimensions of pores and other features of the wipes or sponges, a portion of the organisms to be killed can be drawn into the disinfectant appliance from a wetted surface and/or all or the remaining organisms on the surface can be killed upon forcing $ClO_2$ solution from the appliance. The wipe or sponge can be pressed against a surface or squeezed over a surface to deliver $ClO_2$ solution to the surface where the surface is thereby disinfected by the action of the $ClO_2$ on any virus, bacteria, or fungi on the surface. Depending upon the size of the wipe or sponge, a relatively small surface, such as a wound, a large surface, such as, but not limited to, a table, tray, or instrument, or a portion of a very large surface, such as a wall or floor, can be disinfected using a single wipe. Generally, but not necessarily, the appliance is wetted once.

Figure 9:
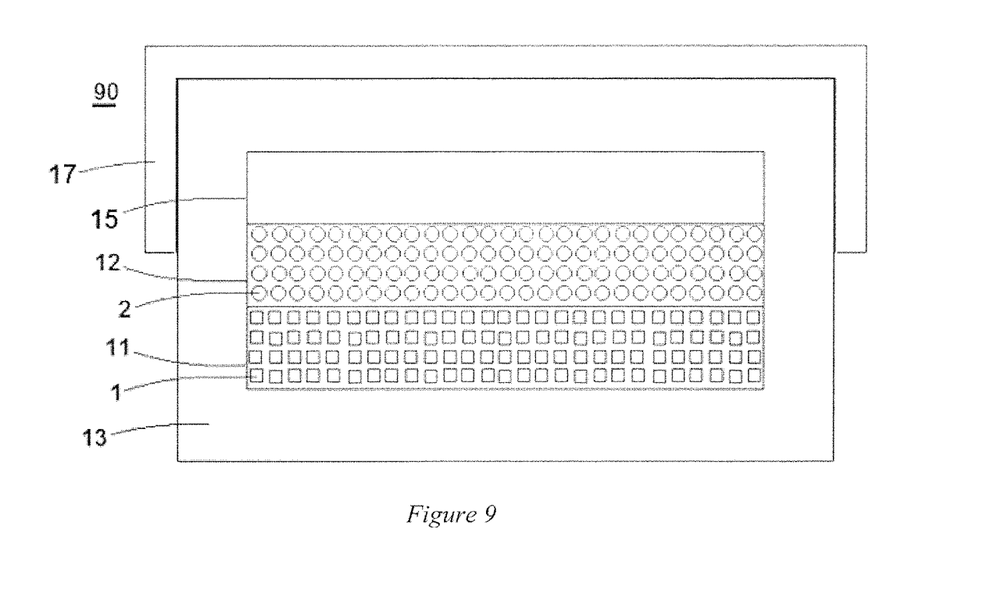
FIG. 9 shows a disinfectant appliance of the structure of FIG. 2 with a handle covering a portion of the surfaces on the proximal side of the storage section, according to an embodiment of the invention.

The redox resin and chlorite absorbent can be dispersed in a plurality of layers or in a single mixed layer where the lack of water or other liquid vehicle prevents the premature contacting of chlorite with the redox resin. An additional $ClO_2$ absorption layer, storage section, can be included. The disinfectant appliance has an outer surface that permits or promotes the flow of water into the other layers. For example, an open cell foam material can encase the other layers to promote the flow of water into the disinfectant appliance and the $ClO_2$ solution from the appliance when pressure is applied to the appliance. The appliance can be shaped with a layer disposition that is appropriate for use when directly held by hand or it can be in a form that fits to a holder that promotes the drawing of water in from one portion of the disinfectant appliance and the expulsion of $ClO_2$ solution from the same or other portion of the disinfectant appliance. In an embodiment of the invention, as shown in FIG. 9, a handle or holder 17 can be attached to the appliance 90 where it is adhered or fused to the appliance as a single unit or the holder can be one that is reversibly attached to a fresh appliance before use and detached from a spent appliance after use. The holder 17 of appliance 90 is situated such that the appliance is placed in contact with water to draw the water up through the surface layer 13 distal to the holder 17 and draw the fluid through the first layer 11, second layer 12, and into the storage section 15 before expelling the $ClO_2$ solution from the water entry space.

Figure 10:
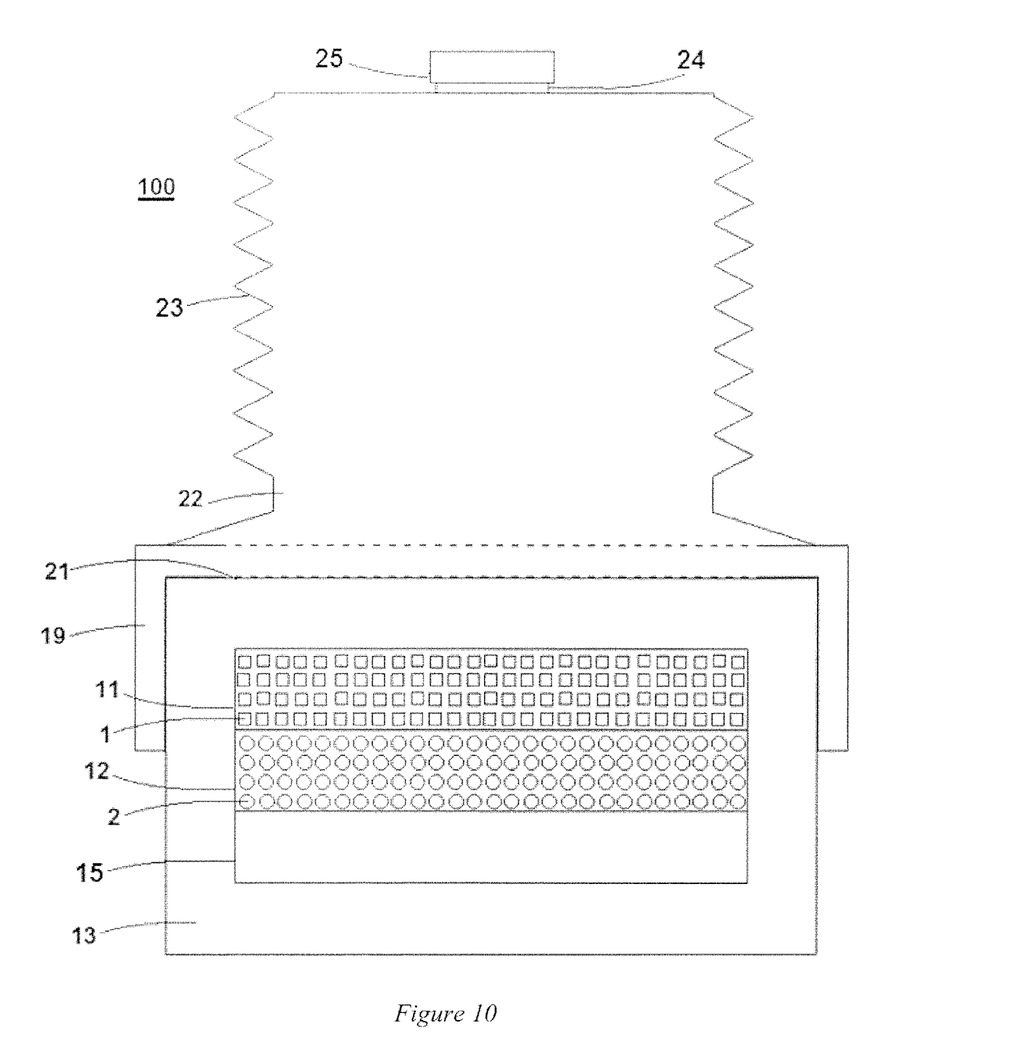
FIG. 10 shows a disinfectant appliance of the structure of FIG. 2 with a handle having a means to infusing water into the appliance covering a portion of the surfaces on the distal side opposite of the storage section, according to an embodiment of the invention.

In another embodiment of the invention, the disinfectant appliance can include a holder that includes a means to infusing water into the appliance where the means directs and controls the fluid flow into and within the appliance. As shown in FIG. 10, appliance 100 includes a handle or holder 18 that includes a reservoir 19 into which water can be placed through an opening 23 that can include a cap 24. A side of attachment of the holder 18 includes a porous surface 21 through which water can drain into the appliance by gravity to promote the fluid flow from the first layer 11 to the second layer 12, and into the optional storage section 14. As illustrated, the walls of the reservoir can be bellows 22, such that when filled with water and a cap 24 is tightened, the reservoir can be compressed to expel the water into the appliance. The holder can be one that is adhered or fused to the appliance or can be reversibly connected to a fresh appliance and disconnected to a spent appliance. Other means of directing and controlling the fluid flow through the appliance can be used, including plungers, squeezable bulbs, or any other means to accept and expel fluid that can be directed specifically to a selected surface of the disinfectant appliance.

All patents and patent applications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

I claim:

1. A disinfect appliance, comprising:
a plurality of chlorite absorbent particles and either a plurality of redox resin particles or a plurality of acid resin particles, and at least one absorbent material, whereby the absorbent material allows infusion of water into the disinfectant appliance, release of chlorite from the chlorite absorbent particles into the water to form a chlorite comprising solution, contacting of the chlorite comprising solution with the redox resin particles, and the expulsion of $ClO_2$ comprising solution from the disinfectant appliance.

2. The disinfectant appliance of claim 1, wherein the chlorite absorbent particles reside in at least one first layer and the redox resin particles or the acid resin particles reside in at least one second layer.

3. The disinfectant appliance of claim 2, wherein the first layer further comprises a first absorbent material selected from the at least one absorbent material.

4. The disinfectant appliance of claim 2, wherein the second layer further comprises a second absorbent material selected from the at least one absorbent material.

5. The disinfectant appliance of claim 1, wherein the chlorite absorbent particles and the redox resin particles or the acid resin particles reside in at least one combined layer.

6. The disinfectant appliance of claim 1, wherein the chlorite absorbent particles comprise a chlorite salt absorbed in an absorbent.

7. The disinfectant appliance of claim 6, wherein the chlorite salt is sodium chlorite, potassium chlorite, lithium chlorite, cesium chlorite, magnesium chlorite, or calcium chlorite.

8. The disinfectant appliance of claim 6, wherein the absorbent is silica gel.

9. The disinfectant appliance of claim 1, wherein the redox resin is a tri-halide anion resin.

10. The disinfectant appliance of claim 9, wherein the tri-halide anion resin comprises an anion exchange resin where the bound tri-halide anion is $Br_3^-$, $Cl_3^-$, $IBr_2^-$, $ICl_2^-$, $BrCl_2^-$, $BrI_2^-$, $ClBr_2^-$, or $ClI_2^-$.

11. The disinfectant appliance of claim 1, wherein at least one of the at least one absorbent material is a foam.

12. The disinfectant appliance of claim 11, wherein the foam is an open cell foam.

13. The disinfectant appliance of claim 11, wherein the foam comprises polyester, polyurethane, polyimide, polyolefin, polydimethylsiloxane, cellulose, or polyvinyl alcohol.

14. The disinfectant appliance of claim 1, wherein at least one of the at least one absorbent material is gel.

15. The disinfectant appliance 14, wherein the gel comprises polyvinyl alcohol.

16. The disinfectant appliance of claim 1, further comprising a storage section, wherein the storage section is a $ClO_2$ solution absorbent selected from the at least one absorbent material.

17. The disinfectant appliance of claim 1, further comprising a holder.

18. The disinfectant appliance of claim 17, wherein the holder is attached to an exterior surface of one of the at least one absorbent material.

19. The disinfectant appliance of claim 17, wherein the holder is detachable from the disinfectant appliance.

20. The disinfectant appliance of claim 17, wherein the holder comprises a means to direct and control the fluid flow.

21. A method of disinfecting a surface, comprising:
providing a disinfectant appliance according to claim 1;
contacting the disinfectant appliance with water;
drawing the water through the chlorite absorbent particles and either the redox resin particles or the acid resin particles;
releasing a chlorite salt from the chlorite absorbent particles to form a chlorite comprising solution;
contacting the chlorite comprising solution with the redox resin particles or the acid resin particles to form a $ClO_2$ comprising solution: and
discharging the ClO2 comprising solution from the disinfectant appliance onto a potentially infected surface, wherein the surface is disinfected.

22. The method of claim 21, wherein containing comprises submerging at least a portion of the disinfectant appliance into the water, pouring water onto at least a portion of the disinfectant appliance; or infusing water into a portion of the disinfectant appliance.

23. The method of claim 21, wherein drawing comprises wicking the water into the disinfectant appliance, optionally, where wicking is promoted by compressing and releasing the disinfectant appliance.

24. The method of claim 21, wherein discharging comprises wicking the water from the disinfectant appliance onto the potentially infected surface, optionally, where wicking is promoted by the disinfectant appliance.

* * * * *